United States Patent [19]

Gaba

[11] Patent Number: 5,601,532
[45] Date of Patent: Feb. 11, 1997

US005601532A

[54] LOCKING SAFETY COVER FOR SHARP INSTRUMENTS

[75] Inventor: Rodolfo Gaba, Simi Valley, Calif.

[73] Assignee: Graphic Controls Corporation, Buffalo, N.Y.

[21] Appl. No.: 583,989

[22] Filed: Jan. 11, 1996

Related U.S. Application Data

[63] Continuation-in-part of Ser. No. 472,553, Jun. 7, 1995, which is a continuation-in-part of Ser. No. 376,399, Jan. 23, 1995, Pat. No. 5,533,974, which is a continuation-in-part of Ser. No. 94,842, Jul. 20, 1993, Pat. No. 5,417,659.

[51] Int. Cl.[6] .................................................. A61M 5/32
[52] U.S. Cl. ................................. 604/110; 206/366
[58] Field of Search .................................. 604/110, 187, 604/192, 263; 206/365, 366

[56] References Cited

U.S. PATENT DOCUMENTS 4,995,871  2/1991  Sasaki et al. ............................ 604/110
5,187,850  2/1993  McCammon et al. ............. 604/110 X
5,417,659  5/1995  Gaba .

Primary Examiner—John D. Yasko
Attorney, Agent, or Firm—Lyon & Lyon

[57] ABSTRACT

A safety device for a medical/surgical needle has a needle retainer in a chassis within a housing. The needle retainer includes a spring pushing a gripping wheel against walls of the chassis. The needle retainer allows a needle point to enter into the chassis, but prevents withdrawal of the needle. A cover slidably positioned over the housing has a conical opening with internal splines. After the needle point is captured within the housing, the cover is moved, as far as is necessary, depending upon the length of the needle, to engage the needle hub. The cover is then turned to unwind the needle from its syringe, while the needle point is safely captured within the housing.

17 Claims, 9 Drawing Sheets

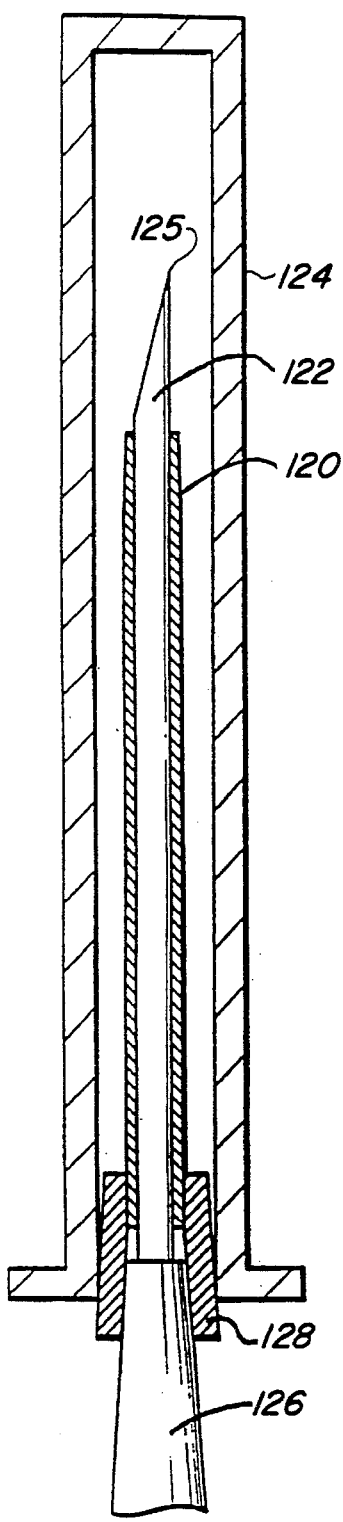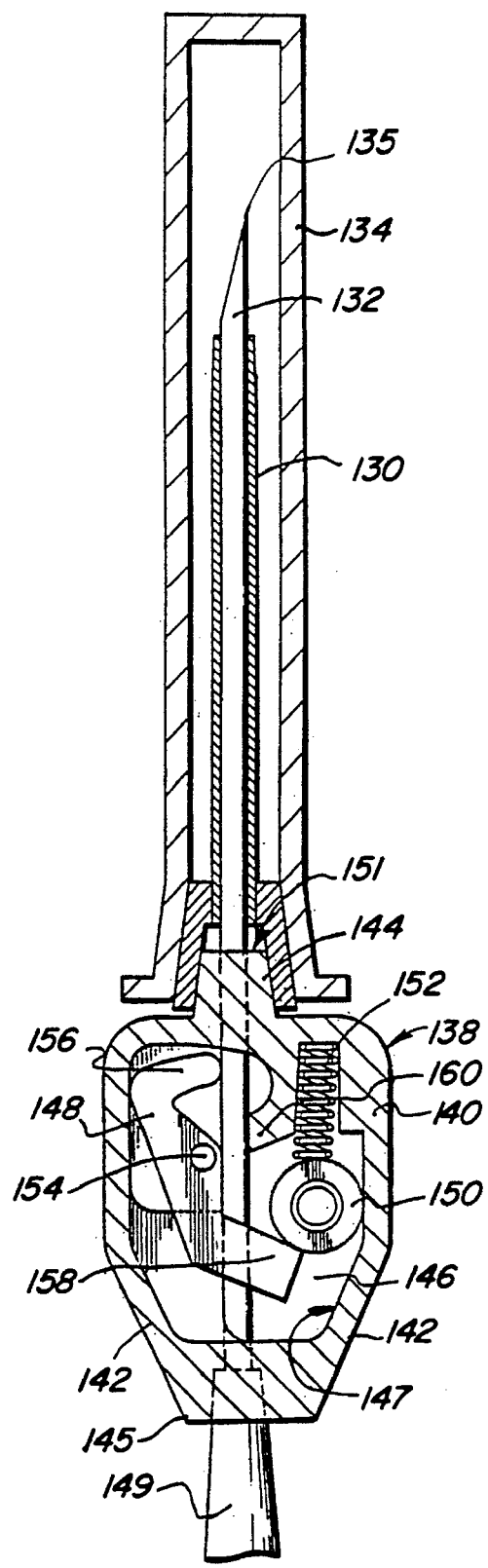
Fig. 7
(PRIOR ART)
Fig. 8

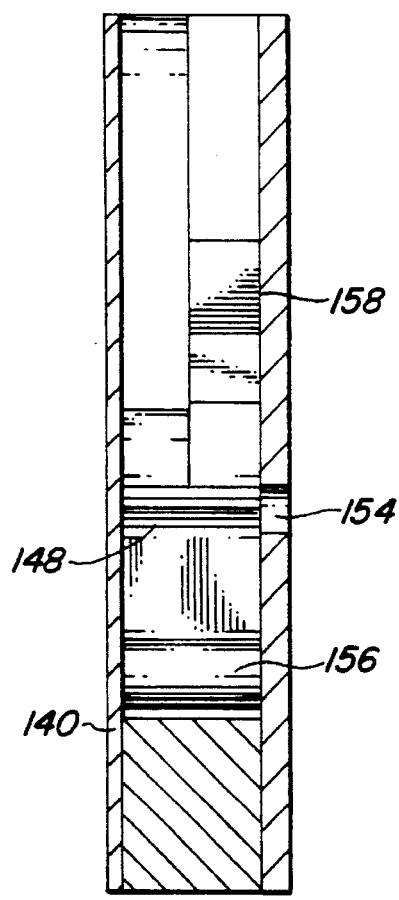
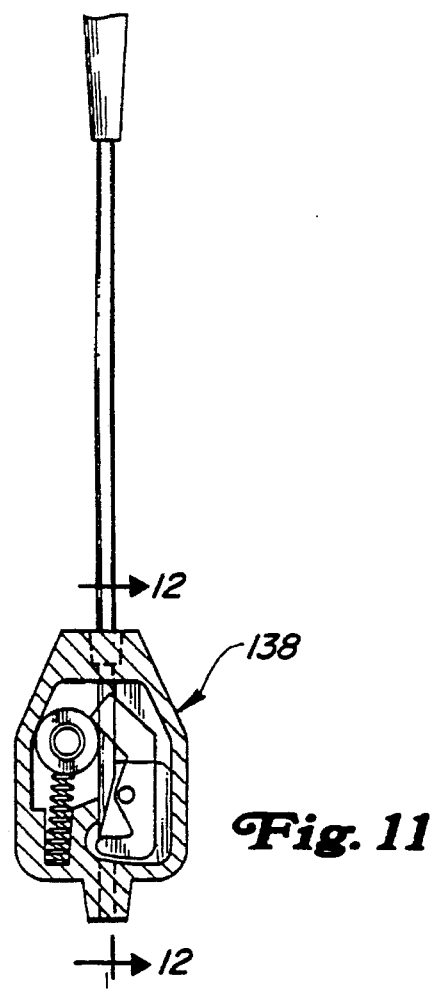
Fig. 11
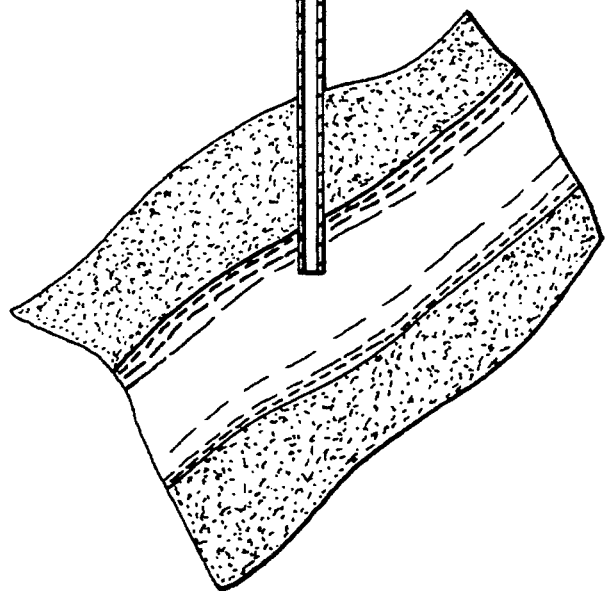
Fig. 12

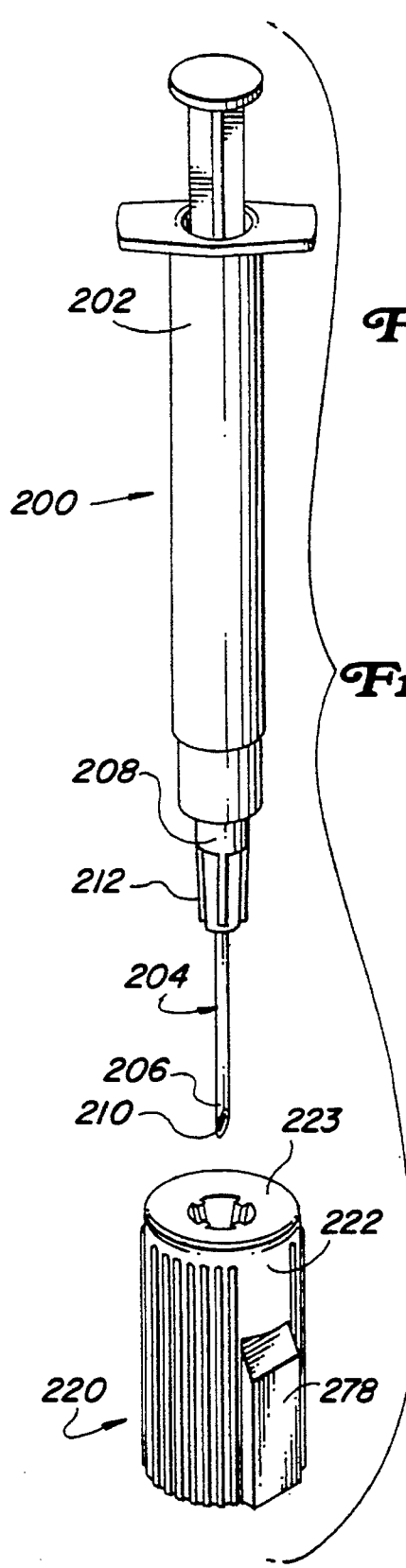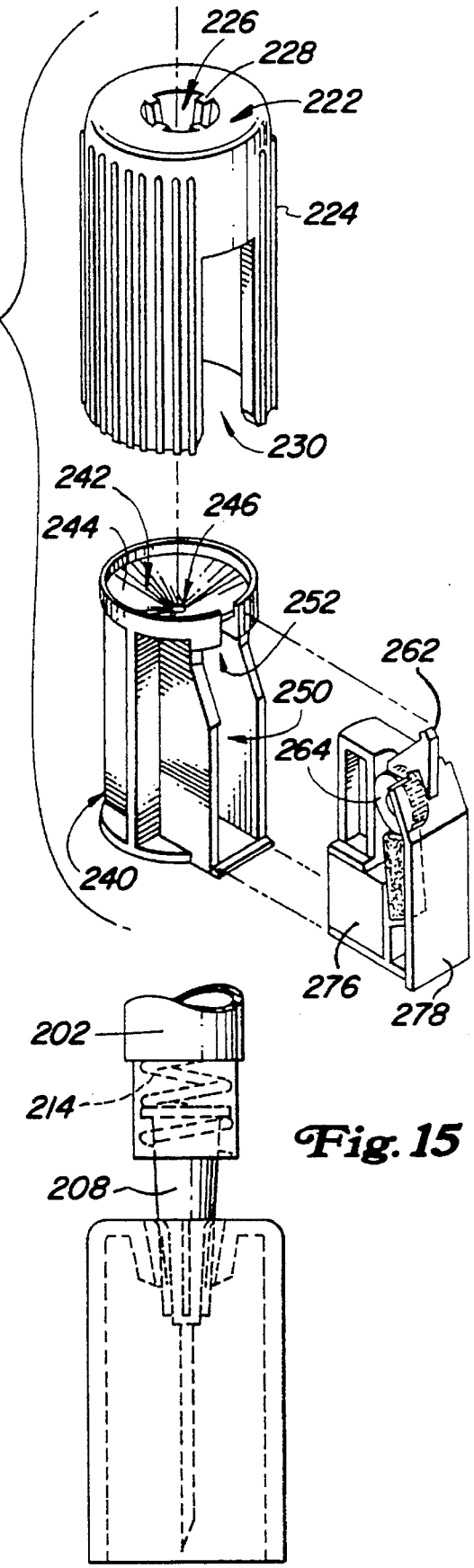

5,601,532

LOCKING SAFETY COVER FOR SHARP INSTRUMENTS

This application is a continuation-in-part of Ser. No. 08/472,553, filed Jun. 7, 1995, and now pending, which in turn is a continuation-in-part of Ser. No. 08/376,399, filed Jan. 23, 1995 and now U.S. Pat. No. 5,533,974, which in turn is a continuation-in-part of Ser. No. 08/094,842, filed Jul. 20, 1993, and now U.S. Pat. No. 5,417,659, all incorporated herein by reference.

BACKGROUND OF THE INVENTION

The invention relates to medical product disposal devices used in hospitals and medical offices, and more particularly to a device for permanently capping the end of disposable surgical sharps such as needles, scalpels, etc. Once used, such sharp instruments pose hazards to nurses, doctors, and to patients, as they are typically contaminated with blood or other bodily fluid.

While various safety devices and containers have been proposed in the past, there remains a need for a device which provides permanent disposal of used surgical sharps, including needles, in a safe, reliable and easy manner.

My U.S. Pat. No. 5,417,659 describes a safety device for permanently capping needles. However, because certain medical procedures require removal of the needle from the syringe, there is a need for the user to be able to safely disengage a needle from the connected syringe after it is used in a medical procedure. While the safety device shown in U.S. Pat. No. 5,417,659 works well, it does not necessarily allow for easy separation of a capped needle from the syringe, especially if the needle is short. Accordingly, there remains a need for an improved safety cover or capping device for needles or other sharp instruments.

SUMMARY OF THE INVENTION

To these ends, a cap or cover for a surgical instrument preferably includes a housing, a gripper for engaging the free end of the sharp or needle, a wedge for engaging the gripper, and a biasing element or spring for urging the wedge and the gripper into engagement.

The wedge advantageously cooperates with the gripper such that, upon insertion of the free end of the sharp into the housing, the gripper exerts a force against the free end. A component of that force is perpendicular to the longitudinal axis of the sharp. Thus, a longitudinal movement of the sharp tending to withdraw the free end of the sharp from the housing causes the component of force perpendicular to the longitudinal axis of the sharp to increase. The sharp is therefore locked against withdrawal from the housing.

To allow the needle and syringe to be separated, the housing preferably has a sliding outer cover with forward internal splines. The splines advantageously engage splines on the free end of a hypodermic needle that is captive in the housing, thus allowing the syringe to be separated from the needle by rotating the cover in relation to the syringe. The captive needle, therefore, may be safely removed from a syringe as required by certain medical procedures.

Accordingly, it is an object of the invention to provide a device for more safely handling used needles or other sharp instruments.

BRIEF DESCRIPTION OF THE DRAWING

In the drawings, wherein similar reference characters denote similar elements, throughout the several views.

FIG. 7 is a partial section view of a conventional IV catheter kit including a catheter, needle, and needle cover;

FIG. 8 is a partial section view of a new IV catheter having a needle lock or cap according to the present invention;

FIG. 11 is a partial section view thereof showing the IV catheter remaining in the patient and with the needle locked into the needle lock and detached from the IV catheter;

FIG. 12 is a section view of the needle lock taken along line 12—12 of FIG. 11;

FIG. 13 is a perspective view of another embodiment used in applications where it is desirable to separate the needle from the syringe, after a procedure;

FIG. 14 is an exploded perspective view thereof;

FIG. 15 is an enlarged partial section view of a needle inserted into the sliding outer cover, with the splines of the needle hub engaged with the splines of the sliding outer cover of the present safety device;

DETAILED DESCRIPTION OF PREFERRED EMBODIMENTS

Figure 2:
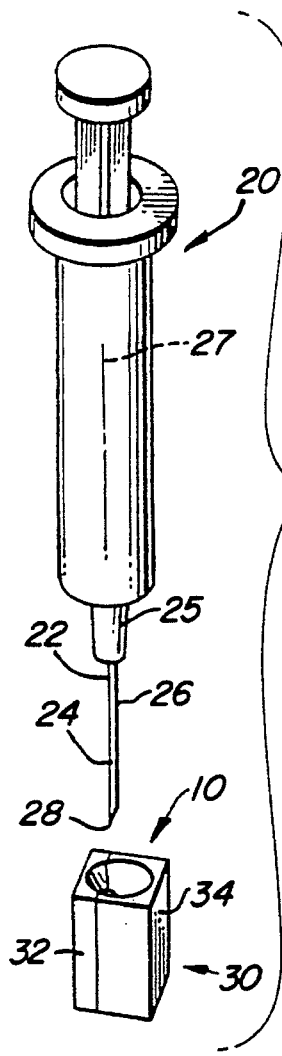
FIG. 2 is a perspective view of the cover or cap of FIG. 1, positioned to receive the free end of a hypodermic needle through a funnel-shaped sharps guide.
Figure 5:
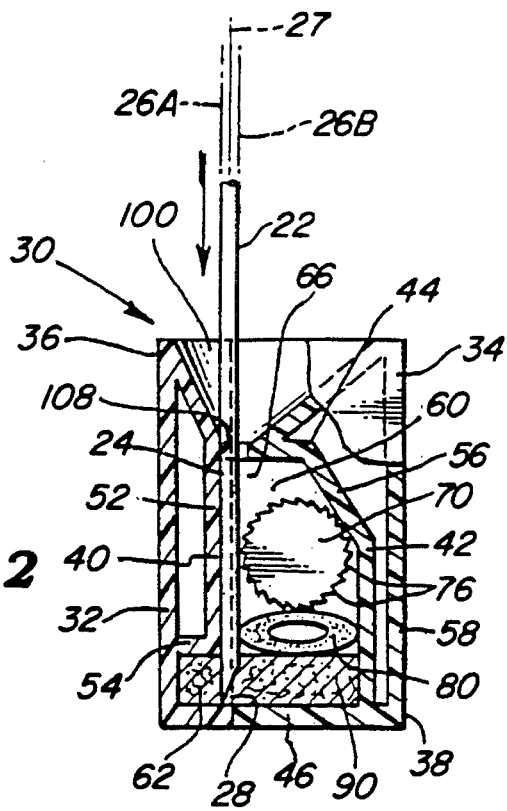
FIG. 5 is a section view similar to FIG. 3, but showing the free end of a needle inserted into the cover.

Referring now to the drawings, as best shown in FIGS. 2 and 5, the present cover 10 is configured to receive and permanently cap the free end of a hypodermic needle, or other sharp. As shown in FIG. 2, a hypodermic syringe and needle assembly 20 includes a needle 22 having a free end 24, a restrained end 25, an outer surface 26, and a longitudinal axis 27. Free end 24 has a sharp tip 28 to pierce the skin and/or tissue.

Figure 1:
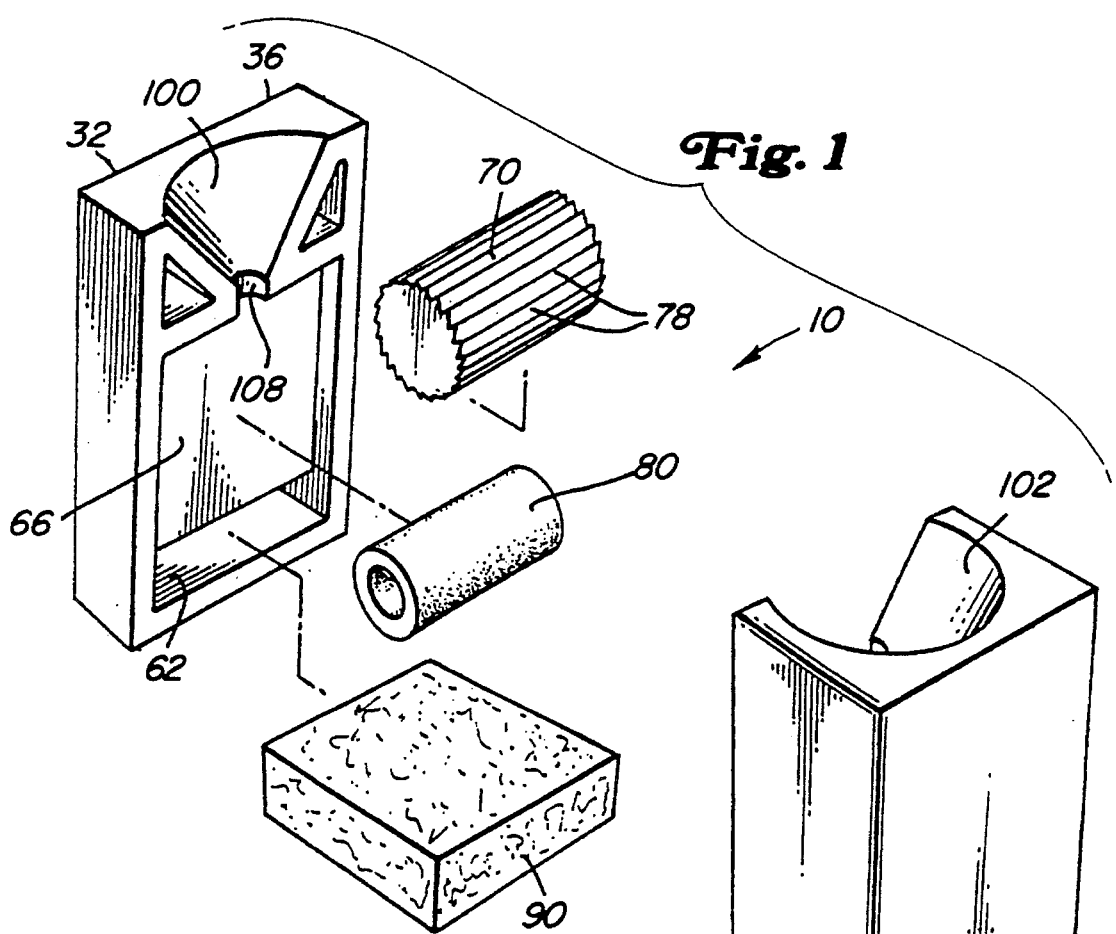
FIG. 1 is an exploded perspective view of a preferred embodiment of the present sharp cover.

Referring now to FIG. 1, the cover 10 includes a housing 30, a gripping element 70, a biasing element 80, and preferably a sealing element 90. The housing 30 is advantageously provided as a two-part plastic assembly having a first section 32 and a second section 34. The housing 30 includes top and bottom ends 36 and 38. A sharps receiving portion 100 is provided at the top end 36. A conical metal liner 101 is attached (bonded, snapped or molded-in, etc.) to the receiving portion 100 to prevent sharp instrument tips from sticking into the plastic receiving portion surface.

Figure 3:
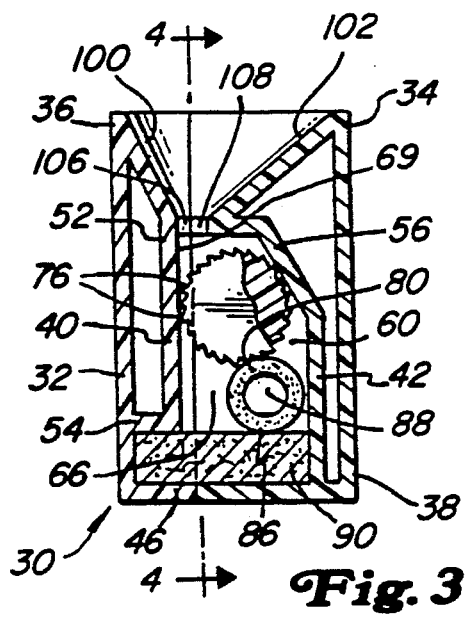
FIG. 3 is a view taken along line 3—3 of FIG. 2.
Figure 4:
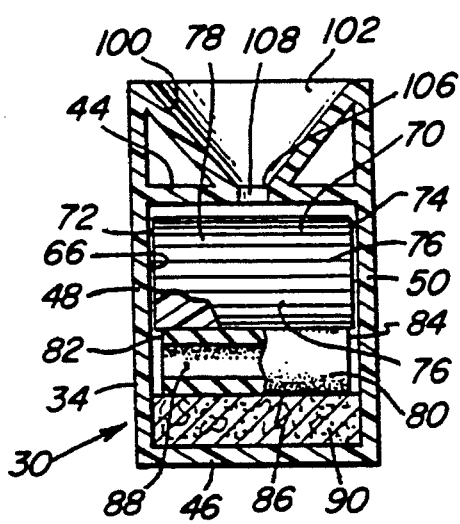
FIG. 4 is a section view taken along line 4—4 of FIG. 3.

As best shown in FIG. 3, the housing 30 is also provided with a first set of substantially opposed lateral interior surfaces 40 and 42, an upper interior surface 44 and lower interior surface 46. As best shown in FIG. 4, the housing 30 also includes a second set of substantially opposed lateral interior sidewalls 48 and 50. Lateral interior surfaces 40 and 42 and interior sidewalls 48 and 50 each extend between upper and lower interior surfaces 44 and 46 to define an interior cavity 60. The gripping element 70, biasing element 80 and sealing element 90 are contained within the cavity 60.

The lateral interior surface 40 includes an upper planar portion 52 and lower portion 54. As best shown in FIG. 5 upper planar portion 52 is configured to engage the free end 24 of the needle along tangent 26A upon insertion of free end 24 into the cover 10. The lower portion 54 defines a recess 62 provided to position the sealing element 90 adjacent the lower interior surface 46. Upon insertion of a needle, the needle tip 28 embeds into the sealing element 90.

The lateral interior surface 42 includes an upper angled portion 56 and a lower planar portion 58. The upper angled portion 56 together with upper planar portion 52 form a wedging element 64 configured to cooperate with the gripping element 70 before and after insertion of free end 24 of the needle into the cover 10. As best shown in FIG. 3, the upper angled portion 56 inclines towards the lateral interior surface 40 as the upper angled portion 56 extends from the lower planar portion 58 towards the first end 36 to define an area of convergence or a wedge zone 66. The lower planar portion 58 is substantially parallel to the upper planar portion 52.

The gripping element 70 is substantially cylindrical in shape, having two flat ends 72 and 74 and a substantially arcuate gripping surface 76. Referring to FIG. 4, the gripping element 70 is positioned within interior cavity 60 with the flat ends 72 and 74 closely adjacent to the interior sidewalls 48 and 50. The distance between sidewalls 72 and 74 is sufficient to permit the gripping element 70 to slide within cavity 60 between the upper and lower interior surfaces 44 and 46, while substantially maintaining its alignment.

Referring now to FIGS. 3 and 5, the dimensions of gripping surface 76 (vis-a-vis wedging element 64 and the needle) are shown proportionally in the drawings and are selected to ensure that gripping surface 76 (in response to the biasing action of biasing element 80) remains in simultaneous engagement with the upper planar portion 52 and the angled portion 56 before insertion of free end 24 of the needle into the housing 30, and to ensure that gripping surface 76 (in response to the biasing action of biasing element 80) remains in simultaneous engagement with the outer surface 26 of the needle along tangent 26B and angled portion 56 after insertion of the needle into the housing 30.

The substantially arcuate gripping surface 76 facilitates the foregoing described purposes while at the same time ensuring that gripping element 70 does not engage the free end 24 of the needle in such a manner as to prevent free end 24 from being fully inserted into the interior cavity 60 as best shown in FIG. 5. It will be understood by those skilled in the art that other configurations of gripping element 70 may also facilitate these purposes.

Preferably, the biasing element 80 is an annular shaped elastomer, having two flat ends 82 and 84, a substantially round outer surface 86, with a hole 88 extending between the ends 82 and 84. As shown in FIG. 4, the biasing element 80 is positioned within the interior cavity 60, between the gripping element 70 and the sealing element 90, such that its ends 82 and 84 are adjacent the sidewalls 48 and 50 and outer surface 86 engages gripping element 70.

Referring now to FIGS. 3 and 5, the outer diameter (uncompressed) of the biasing element 80 is sufficiently large to ensure that it constantly acts upon the gripping element 70, urging the gripping element 70 towards the first end 36. This causes the gripping surface 76 to engage the upper planar portion 52 and the angled portion 56 as described above.

Assembly of the cover 10 is accomplished by compressing outer surface 86 of the biasing element 80 sufficiently to enable the gripping element 70, the biasing element 80 and the sealing element 90 to be inserted into interior cavity 60. Thereafter, first and second sections 32 and 34 of housing 30 are joined together using any conventional methods.

The interaction between the biasing element 80, the gripping element 70 and the wedging element 64 prior to insertion of free end 24 into interior cavity 60 is shown in FIG. 3. The biasing element 80 exerts an upward force on the gripping element 70. This upward force drives the gripping element 70 into engagement with the upper planar portion 52 and the angled portion 56, effectively wedging the gripping element 70 therebetween. The pressure exerted against gripping element 70 at the interface between gripping element 70 and angled portion 56 includes a component of force which is perpendicular to the upper planar portion 52. This component of force is offset by an opposing force at the interface between the gripping element 70 and the upper planar portion 52.

As the free end 24 of the needle is inserted into interior cavity 60, it is wedged between the upper planar portion 52 and the gripping element 70 thereby displacing gripping element 70 and causing the gripping element 70 to move downwardly towards the bottom end 38. As shown in FIG. 5, the free end 24 is engaged by the upper planar portion 52 along tangent 26A and engaged by the gripping element 70 along tangent 26B. The downward motion of gripping element 70 causes biasing element 80 to further compress thereby increasing the amount of pressure exerted by the biasing element 80 against the gripping element 70. This in turn increases the pressure at the interface between the gripping element 70 and the angled portion 56 which, in turn, increases the pressure at the interface between the upper planar portion 52 and the free end 24 along tangent 26A and at the interface between the gripping element 70 and free end 24 along tangent 26B.

Any attempt to withdraw needle 22 from the interior cavity 60 after insertion will generate opposing frictional forces at the interface between the upper planar portion 52 and free end 24 and at the interface between gripping element 70 and free end 24. The frictional force exerted by free end 24 upon gripping element 70 will tend to drive gripping element 70 upwardly towards the first end 36 thereby increasing the pressure exerted against the gripping element 70 at the interface between the gripping element 70 and the angled portion 56 which, in turn, will increase the pressure exerted both at the interface between the upper planar portion 52 and free end 24 along tangent 26A and at the interface between the gripping element 70 and free end 24 along tangent 26B, thereby increasing the needle retaining effect of the cover 10. The greater the force applied to needle 22 tending to withdraw the free end 24 from the interior cavity 60, the greater the frictional forces exerted upon the free end 24 resisting such movement. The needle therefore becomes permanently locked within the housing.

The biasing element 80 is selected to allow surgical sharps to be manually inserted into the interior cavity 60 without difficulty while at the same time ensuring that any attempt to withdraw such sharp will be opposed by sufficient frictional forces as described above. While, in the preferred embodiment, the biasing element 80 must be sufficiently large to render the cover 10 operable, the biasing element 80 must not be so large or stiff as to prevent the needle 22 from being inserted into interior cavity sufficiently to ensure that tip 28 fully engages sealing element 90. Preferably, the outer diameter 87 (compressed) of the biasing element 80 as measured in a plane transverse to upper planar portion 52 must be less than the distance between the tangent 26B to outer surface 26 and lower planar portion 54. To further facilitate complete engagement of the tip 28 and sealing element 90, the biasing element 80 may be positioned within the interior cavity 60 vis-a-vis the gripping element 70 such that the pressure at the interface between gripping element 70 and the biasing element 80 urges the biasing element 80 away from the upper planar portion 52, as shown in FIG. 5. Those skilled in the art will understand that alternative configurations, compositions and placements of biasing element 80 are possible and that alternative means may be employed to ensure that biasing element 80 does not unduly impede insertion of free end 24 into foil 10.

Figure 6:
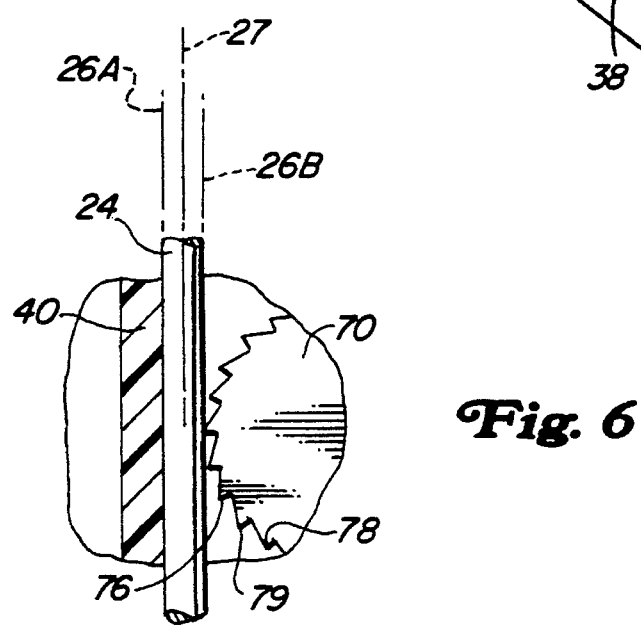
FIG. 6 is an enlarged partial section view of the cover of FIG. 5 showing a preferred gripper in engagement with a the needle after attempted withdrawal of the needle.

The needle retaining effect of the foregoing describe design is enhanced by the provision, on the gripping surface 76, of a plurality of evenly-spaced teeth 78, each of which extends between ends 72 and 74. The teeth 78 provide sharp edges 79 and are backwardly curving, as best shown in FIG. 6, to improve the gripping characteristics of the gripping surface 76. The teeth 78 (and the rest of gripping element 70) are preferably composed of a material which is hard enough to gouge the outer surface 26 of free end 24. As a result, attempts to withdraw the needle 22 from interior cavity 60 drive the teeth 78 into the outer surface 26 thereby creating a mechanical interference which precludes withdrawal of the needle 24. The free end 24 of the needle 22 is thus permanently locked into the cover 10. The gripping surface 76 and upper planar portion 52 may, alternatively, be roughened or scored to improve the needle retaining effect.

To guard against the hazardous and uncontrolled accumulation of bodily fluids which may reside within used sharps, e.g., hypodermic needles, the cover 10 is also provided with sealing element 90. Upon insertion of free end 24 of the needle 22 into the interior cavity 60, the tip 28 engages and becomes embedded within the sealing element 90 thereby retaining any such residual bodily fluids within the interior of the needle 22. Preferably, the sealing element 90 is a slab of material which is sufficiently soft to allow penetration of tip 28 into the sealing element 90 while at the same time providing a proper seal of the needle tip. In the preferred embodiment, the sealing element 90 is sized to complement the lower interior surface 40 and to reside with the recess 62. The needle port 108 is positioned over the sealing element 90, so that the needle tip will project into the sealing element.

The housing 30 is provided with a sharps receiving portion 100 at its first end 36. As shown in FIGS. 2, 3, and 4, the sharps receiving portion 100 includes sharps guide 102 having a funnel-shaped recess with a maximum diameter 104 on the top end 36 and a minimum diameter 106 at the bottom of the funnel-shaped recess. The minimum diameter 106 defines an eccentric needle port 108 which is sized to receive the free end 24 of a needle 22. The needle port 108 is positioned such that upper planar surface 52 is tangent to the outer diameter of needle port 108. The free end 24 of the needle can accordingly be placed through the needle port 108 without difficulty while simultaneously being properly positioned within the interior cavity 60 between the upper planar portion 52 and the gripping element 70.

A plurality of covers 10 may be mounted in an array on a flat bottom container which can be placed on a surgical table, cart, etc. The bottom end 38 of each cover 10 may be attached to the container, using any suitable means, so that the sharps receiving portion 100 of each cover 10 is directed substantially upward. Alternatively, the container may present the sharps receiving portions 100 at an angle to the horizontal. The bottom of the covers container may be provided with an adhesive or other suitable means to resist unwanted movement during use.

In an alternative embodiment, a safety catheter is provided having similar advantages. As shown in FIG. 7, a needle 122 is surrounded by a conventional IV catheter 120, and covered by a removable needle cap 124. A male fitting 126 on the needle 122 typically engages a female fitting 128 (e.g. a Luer fitting) on the catheter 120, as is well known in the art.

In use, the cap 124 is first removed to expose the point 125 of the needle 122. The needle point 125 is used to puncture the patient's skin, and the needle 122 and catheter 120 are then slowly pushed into the puncture site. The catheter 120 is then held in place within the puncture site while the needle is withdrawn. When the needle has been completely withdrawn, the catheter remains in the patient, and is connected to an IV tube. However, the needle poses a needle stick hazard until it is properly disposed of.

The present safety catheter greatly reduces the needle stick hazard associated with IV catheters. As shown in FIG. 8, the present safety catheter includes an IV catheter 130 and needle cap 134, which may be the same as the conventional catheter and needle cover shown in FIG. 7. The IV catheter 130 is fitted onto a needle lock 138 having a housing 140. The outer surface of the housing 140 may be smooth or knurled. As shown in FIG. 8, the housing 140 has a polygonal shape which includes two tapered surfaces 142. These tapered surfaces 142 provide thumb and finger surfaces for grabbing and holding the housing 140 in place.

The housing 140 includes a fitting 144 similar to the fitting 126 of the conventional catheter needle shown in FIG. 7, for joining the housing 140 and IV catheter 130. Within the housing 140 a stay 160 projects from the housing wall and contacts a needle 132 which extends entirely through the housing 140 and IV catheter 130. An inner wall 147 slants toward the needle 132 at the top of the housing (The safety catheter in FIG. 8 is shown inverted). The needle 132 may be similar to, but is longer than the needle 122 shown in FIG. 7.

A cam 148 within the housing 140 includes a lower leg 156 and an upper leg 158, and pivots on a pin 154. As shown in FIG. 12, the width of lower leg 156 is approximately the same as the interior space 146 within the housing 140. The upper leg 158 is about one half as wide or thick as the lower leg, so that the needle 132 may extend underneath the upper leg 158. The full width of the lower leg 156 prevents the needle 132 from extending into the opening 151, unless the cam is positioned out of the way, as shown in FIG. 8.

A gripping wheel 150 is positioned within the housing 140 between the upper leg 158 of the cam 148, the housing wall, and a spring 152. Preferably, the gripping wheel 150 is formed of metal, hard plastic, or other substantially noncompressible material. The perimeter of the wheel 150 is knurled, roughened or serrated. The wheel 150 is too wide to pass underneath the upper leg 158 of the cam 148. The spring 152 positioned within a spring bore in the housing, pushes the wheel 150 against the upper leg 158. The gripping wheel 150 itself is not attached to any portion of the housing 140. Rather, it is held in place by the spring 152, the upper leg 158 and the housing wall, and can shift position.

When the needle lock 138 is in the position shown in FIG. 8, the spring 152 pushes against the gripping wheel 150. The spring force presses the gripping wheel against the upper leg 158 of the cam 148, causing the cam 148 to rotate about pivot 154 in a clockwise direction, until the lower arm 156 contacts the needle 132 and presses against it. A slight frictional force is thus created between the cam 148, the stay 160, and the needle 132, which helps to prevent the needle 132 from prematurely backing out of the needle lock.

Figure 9:
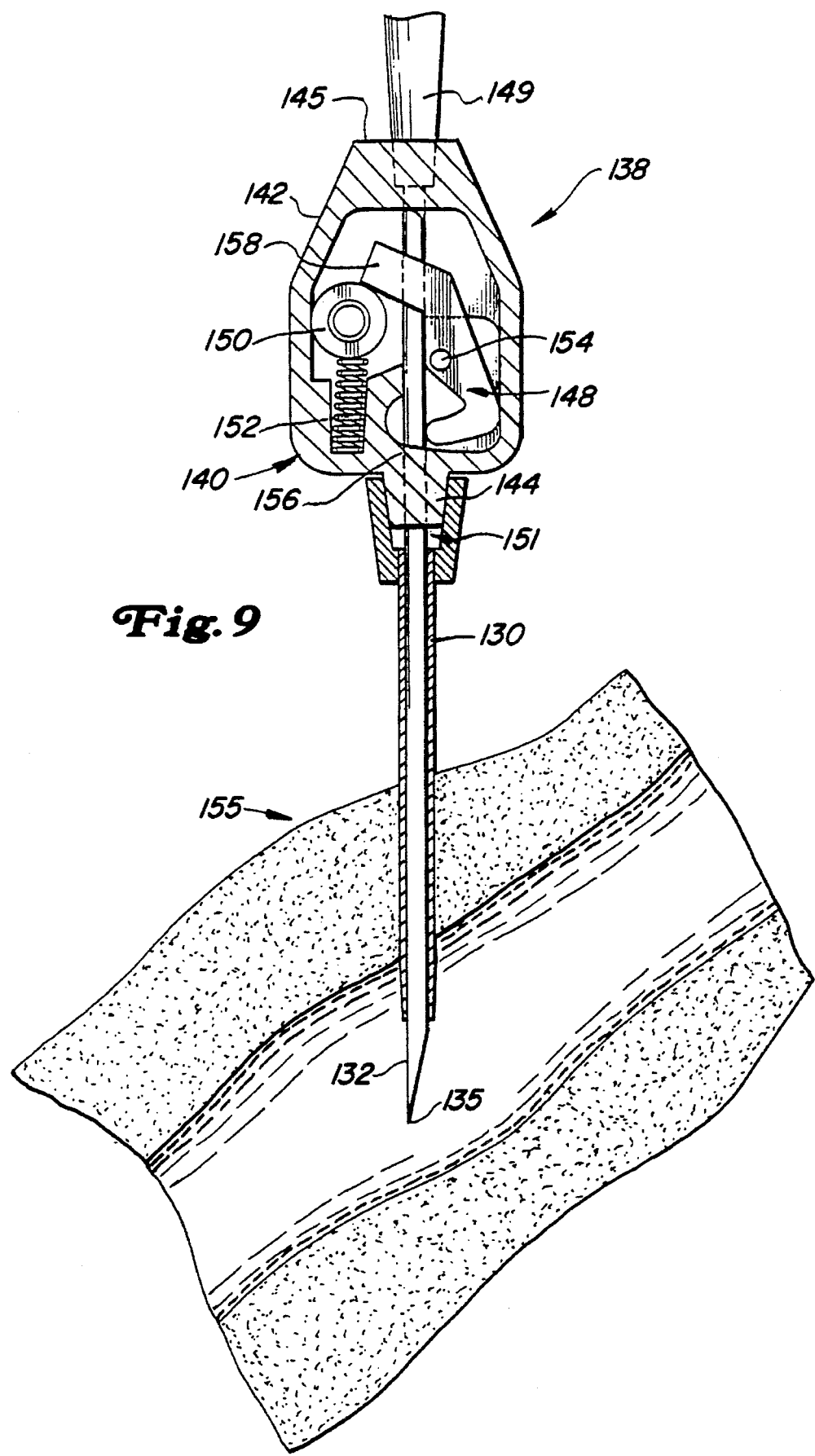
FIG. 9 is a partial section view of the present IV catheter and needle inserted into a patient.

In use, the needle cover 134 is first removed to expose the needle 132. The needle and catheter are then inserted into a patient's arm 155 or other body area, as with conventional IV catheter kits, as shown in FIG. 9.

The needle lock housing 140 is held preferably by clasping the tapered surfaces 142 of the housing between the thumb and forefinger of one hand. With the housing held in place, the needle 132 is withdrawn from the catheter 130. The catheter may optionally be taped down onto the skin.

Figure 10:
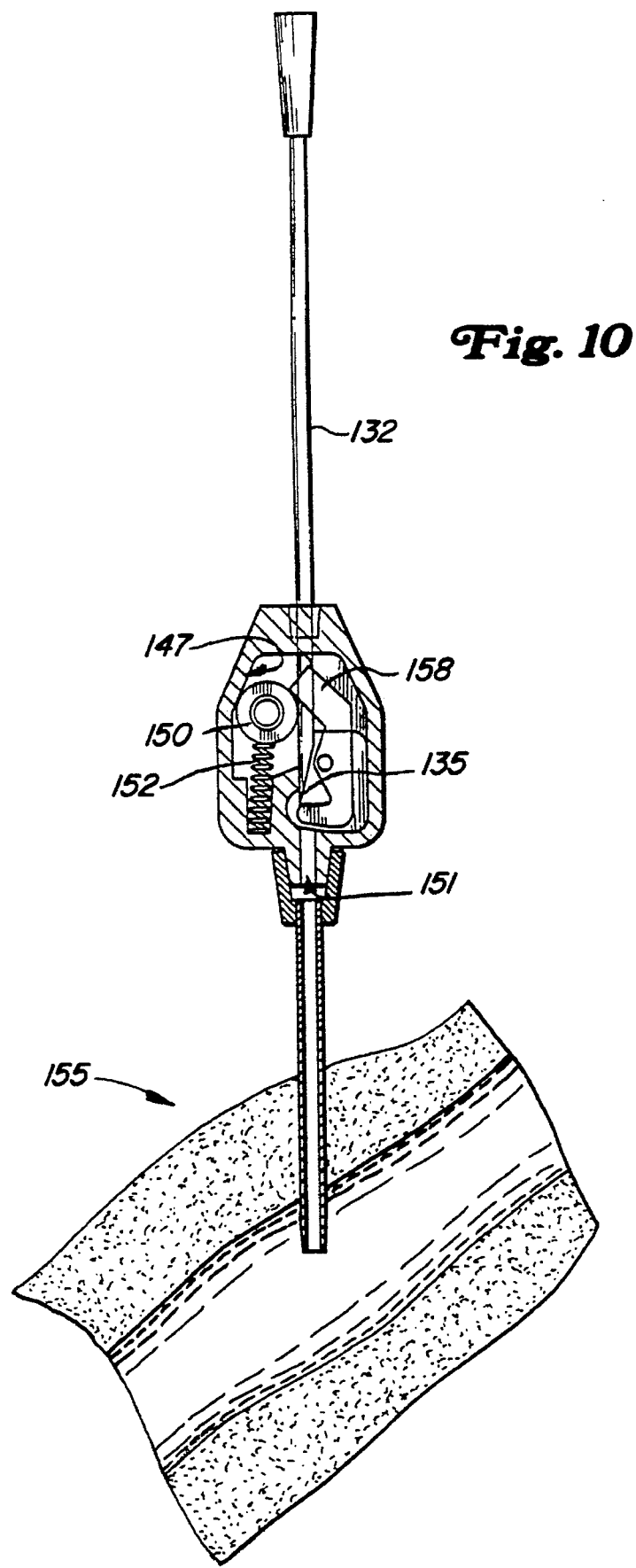
FIG. 10 is a partial section view thereof with the needle point retracted into the needle lock.
Figure 16:
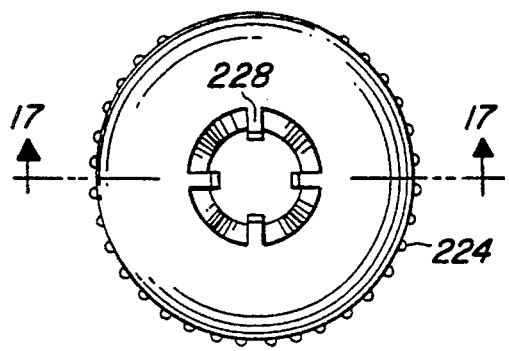
FIG. 16 is a top view of the sliding outer cover shown in FIGS. 13–15.

As the point 135 of the needle 132 is pulled back into the housing 140 and passes the lower leg 156 of the cam 148, the shaft of the needle 132 no longer stops the rotation of the cam 148 about the pivot 154. The force of the spring 152 against the gripping wheel 150 and the upper leg 158 cause the cam 148 to pivot in a clockwise direction. This movement causes the lower leg 156 to move into a position to block the lower opening 151 of the housing 140, as shown in FIG. 10. At the same time the gripping wheel 150 shifts upwardly along the slanted wall 147 and wedges between the shaft of the needle 132 and the wall 147. The spring 152 holds the gripping wheel 150 in this wedged position. The knurled perimeter of the wheel 150 grips the shaft of the needle 132 and the slanted wall 147, preventing the wheel from turning counter clockwise. As the wheel is engaged to both the needle shaft and the wall 147 and cannot turn, the needle 132 cannot be pulled any farther out of the housing. (The geometry allows the wheel to turn or roll clockwise, allowing the needle to be pushed further through the housing, but not counter clockwise, which would allow the needle to be withdrawn.) After the wheel 150 wedges into position as shown in FIG. 10, the cam 148 is prevented from pivoting in a counter-clockwise direction, to release the needle point 135, as the wedged wheel 150 blocks movement of the upper leg 158. Thus the lower leg 156 is locked in a position which blocks the opening 151 preventing the needle 132 from being pushed out of the housing 140, and the wedged wheel prevents the needle from being pulled out of the housing. The needle is therefore locked in position. Before the needle is withdrawn, the upper leg 158 prevents the wheel from shifting up into the wedged position, as shown in FIG. 8.

When the needle is securely locked in position, the point of the needle is safely contained within the housing 140. In addition, once the needle has been retracted into the housing, the cam 148 and gripping wheel 150 prevent the needle from either being pulled out of or pushed through the housing 140. The point of the needle is securely and permanently held within the housing reducing the possibility of injury caused by contact with the used needle.

As shown in FIG. 11, after the needle 132 has been retracted into the housing 140, the fitting on the housing 140 may be disengaged from the catheter 130 and an IV connected. The disengaged needle 132 and needle lock 138 may then be safely disposed of, without replacing the needle cap 134.

The present embodiment therefore provides a safe, efficient and self-contained catheter for protecting the points of used IV needles. Moreover, the needle lock 138 works automatically with the withdrawal of the needle from the IV puncture site. Even if the needle is pulled out of the puncture site very quickly or forcefully, the point 135 will still become locked within the housing 140. The needle lock 138 permits medical personnel to simply insert the needle and catheter, withdraw the needle, and immediately dispose of the used needle without substantial risk of injury, and without the taking of time and risks of recapping or other steps. In addition, the needle lock 138 can be used with standard existing catheters. Standard needles may also be used, if they are long enough to extend through both the catheter 130 and needle lock 138. The needle lock 138 is also highly tamper resistant. Once the needle 132 becomes locked within the housing 140, it is exceptionally difficult or impossible to remove the needle.

Preferably, the housing 140 is made with a thin, flat profile, so that the housing 140 may be laid flat against the patient's skin while the catheter is inserted. For convenience and ease of disposal, the housing 140 should be compact and made of a tough material, preferably metal or a hard plastic. The openings in the housing 140 through which the needle 132 passes should be made to approximate the diameter of the needle itself, to insure that the needle is securely held within the housing 140.

Referring to FIG. 13, in certain procedures, such as blood gas sampling, blood is withdrawn with a hypodermic syringe and needle assembly 200. However, rather than discarding the entire needle assembly 200 (as is often the case in giving injections), the needle 204 must be removed from the syringe 202. As the shaft 206 of the needle 204 is often very short, there may be little space for the medical technician's fingers to grasp, turn and remove the needle 204 after the shaft 206 of the needle 204 is fully inserted into a safety device, such as the housing 30 shown in FIG. 2.

To better provide for separating the needle 204 from the syringe 202, as shown in FIGS. 13–19, a safety device 220 has an outer cover 222 slidably positioned over a housing 240. The cover 222 has longitudinal ribs 224 around its outside circumference. An opening 226 at the top or front of the cover 222 has splines 228 which taper inwardly along a conically tapering inner surface 232. The cover 222 has a housing slot 230, to provide clearance for a ridge section 278 on the housing 240, when the cover is positioned fully over the housing 240, as shown in FIG. 13.

Referring to FIG. 14, the housing 240 has a conical dish surface 242 having a metal liner 244 attached (e.g., bonded shaped or molded in) to the dish surface 242. A needle opening 246 extends through the center of the dish surface 242 and liner 244. The housing 240 has a chassis slot 250 on one side, with a tab slot 252 above the chassis slot 250.

Figure 19:
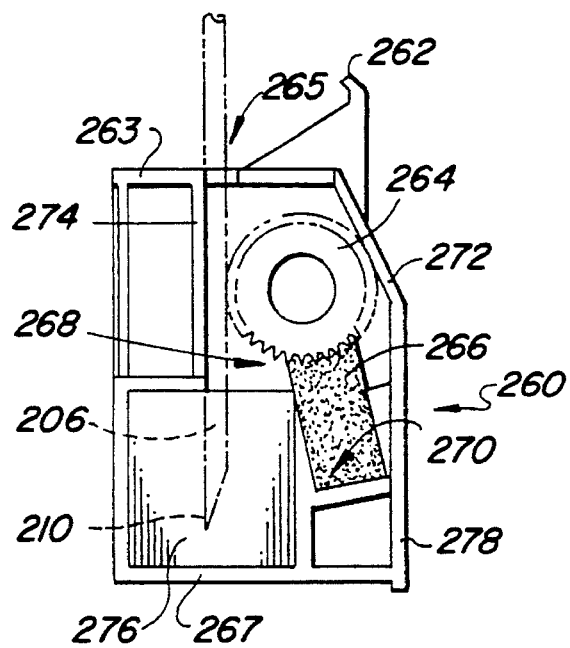
FIG. 19 is a side elevation view of the housing.

Turning to FIGS. 14 and 19, a chassis 260 (preferably molded as a single plastic unit) has a tab 262, a straight wall 274 and an inclined wall 272, in part forming a wheel recess 268. A gripping wheel 264 is positioned within the wheel recess 268. A spring 266 is supported within a spring slot 270 formed by internal chassis walls. The gripper wheel 264 is preferably a steel wheel having a knurled or roughened surface around its circumference (e.g., a cigarette lighter wheel). The spring 266 is advantageously a soft rubber block.

Figure 20:
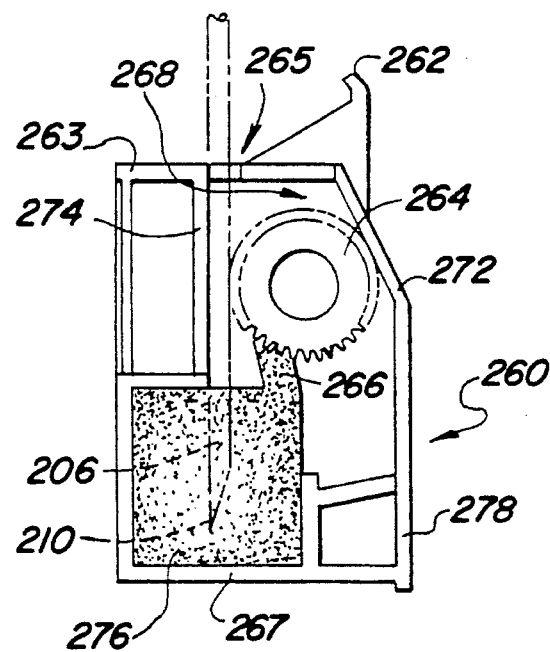
FIG. 20 is a side elevation view of an alternative embodiment having a combined spring and seal block.

A seal block 276 is contained within the chassis 260 and held in place by chassis walls. The seal block is preferably a soft rubber or plastic material. Preferably, the spring 266 and seal block 276 are combined as a single integral piece, with the spring 266 formed as a protrusion on the block 276, as shown in FIG. 20. The chassis 260 has a top wall 263 having a needle entry opening 265 adjacent to the straight wall 274. With the chassis 260, housing 240 and cover 222 assembled and ready for use, as shown in FIG. 13, the opening 226 in the cover 222; the opening 246 in the housing 240; and the opening 265 in the chassis, are aligned, so the needle point 210 can pass freely through them, in between the straight wall 274 and the gripping wheel 264, and into the sealing block 276. The substantially impenetrable lower wall 267 of the chassis 260 prevents the point 210 from piercing through the chassis.

Figure 17:
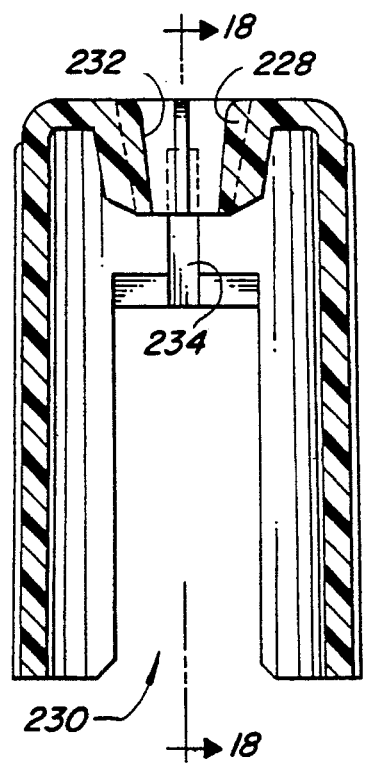
FIG. 17 is a section view of the sliding outer cover taken along line 17—17 of FIG. 16.
Figure 18:
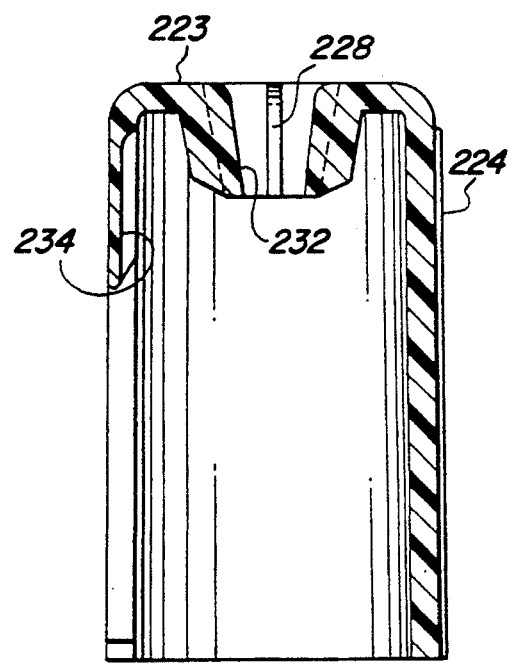
FIG. 18 is a section view of the sliding outer cover taken along line 18—18 of FIG. 17.

Turning to FIGS. 17 and 18, a recess 234 is formed on the inside of the cover 222 above the housing slot 230, and is adapted to receive the tab 262 on the chassis 260.

The cover 222 is provided with splines 228 preferably matching the number of splines 212 on the hub 208 of the needle 204 (FIG. 13). The splines 228, as shown in FIGS. 13, 16, 17 and 18, are spaced apart and oriented to properly intermesh with the splines 212 on the needle hub 208. Typical needles 204 have 4 splines 212. Hence, the cover 222 is also provided with 4 splines 228, although other numbers and configurations may be provided to work with different needles.

In use, the point 210 of the needle 204 is inserted through the opening 226 in the cover 222, through the needle opening 246, and into the chassis 260 wherein it is engaged and locked by the interaction of the wheel 264, spring 266, straight wall 274 and inclined wall 272, as described above in connection with e.g., FIGS. 3, 4 and 5. The device 220 is preferably held in a tray or other fixture during needle insertion, to keep hands away from the needle point. Referring to FIG. 13, with the needle 204 fully inserted, there is little or no clearance between the hub 208 of the needle 204 and the front or top surface 223 of the cover 222. Accordingly, ordinarily, it may be difficult to grasp and turn the hub 208 to remove the needle 204 from the syringe 202. However, as the cover 222 is separate from the housing 240 and chassis 260, the cover 222 can be moved upwardly along the shaft 206 of the needle 204, while the housing 240 remains around and captivates the point 210 of the needle 204 towards the hub 212. The splines 228 and tapered surface or inlet 232 on the cover 222 are configured to match and engage the hub 208 and its splines 212. With the cover 222 engaged onto the hub 208, the cover may be turned (counterclockwise) to unwind the hub 208 from the syringe threads 214 at the lower end of the syringe 202. Accordingly, the needle 204 (i.e., the hub 208 and shaft 206) may be separated from the syringe 202 while the point 210 of the needle 204 is captive within the housing 240, to avoid accidental needle sticks.

If the needle is very short, for example, if the needle shaft 206 is approximately the same length as the height of the housing 240, the cover 222 may engage the needle hub 208, even before the point 210 bottoms out in the seal block 276. In this instance, the cover 222 need not (and cannot) be slid towards the syringe 202 to engage the hub 208. Rather, the needle 204 is unwound simply by holding the syringe 202 and turning the cover 222 (with the housing 240 containing the chassis 260 turning with the cover 222). On the other hand, if the shaft 206 of the needle 204 is longer, the point 210 will bottom out within the seal block 276 while the hub 208 is spaced away from the cover 222. In this situation, the cover 222 is pushed up the along the needle shaft to engage the hub 208. If the needle shaft 206 is exceptionally long, the cover 222 will be moved far enough that it comes completely off of the housing 240, which remains around the point 210. Whether this occurs or not does not affect the operation of the device 220, as the needle 204 is still readily unwound from the syringe 202 while the point 210 is captive in the housing 240. In addition, as the cover 222 cannot fit over the hub 208, after the syringe 202 is separated from the needle 204, the needle 204, cover 222 and housing 240 necessarily remain together.

The tab 262 on the chassis 260 fits within the recess 234 on the cover 222, to act as an additional anti-rotation device between the cover 222 and the housing 240 (in addition to the interaction of the bridge 278 against the side walls of the housing slot 230 on the cover 222) although whether the housing 240 turns with the cover 222 when the needle 204 is unwound, does not affect performance of the device 220.

Although the present invention has thus been described in detail with regard to the preferred embodiment and drawings thereof, it should be apparent to those skilled in the art that various adaptations and modifications of the present invention may be accomplished which still fall in the scope and spirit of the present invention. In particular, it will be appreciated by those skilled in the art that the surgical sharps contemplated for use with the present invention include conventional surgical implements which vary in size and shape depending upon the surgical application including without limitation trocars, stylers, blades and the like. Similarly, while the present invention contemplates the wedging of the free end of surgical sharp between a gripping element and a portion of wedging element, those skilled in the art will appreciate that alternative configurations of wedging, biasing, and gripping may be used as equivalents to those shown and described. Embodiments having pairs of gripping elements, separated by a spring or biasing element, can also be used. With minor modifications, various sharps can be accommodated, such as flat blades, angled or curved blades or needles, etc., as equivalents to the described embodiments. Accordingly, the scope of the present invention should not be limited to the specific embodiments illustrated, but is limited only by the following claims and their equivalents.

What is claimed is:

1. A safety device for capping the point of a needle, comprising: a housing; a needle retainer with the housing and including a wheel and a spring biasing the wheel towards two intersecting walls; and a cover on the housing, the cover having an opening adapted to engage a hub on the needle.

2. The safety device of claim 1 wherein the opening on the cover has a conically tapering inner surface.

3. The safety device of claim 1 further comprising a plurality of splines in the opening on the cover.

4. The safety device of claim 1 wherein the cover is slidably displaceable over the housing.

5. The safety device of claim 1 further comprising a chassis within the housing, with the needle retainer within the chassis.

6. A safety device for a needle comprising:

a housing having a top wall including a needle opening;

a chassis within the housing, the chassis having a straight wall, an inclined wall forming an acute angle with the straight wall, a gripping wheel and a spring urging the gripping wheel towards the straight wall and the inclined wall; and a cover slidably positioned over the housing, the cover having a conically tapering inlet aligned with the needle opening, and a plurality of splines on the inlet.

7. The safety device of claim 6 wherein the chassis is slidably positioned within a chassis slot in the housing.

8. The safety device of claim 6 further comprising a bridge section on the housing and a bridge slot on the cover.

9. The safety device of claim 8 wherein the bridge section comprises the inclined wall.

10. The safety device of claim 6 further comprising a tab on the chassis positioned within a tab slot on the cover.

11. A safety device for a needle having a hub comprising:

a housing;

needle retaining means for retaining a needle point within the housing;

a cover slidably positioned over the housing; and needle hub engaging means on the cover for engaging the hub on the needle.

12. A safety device for a syringe and needle, with the needle having a hub, comprising:

a housing;

a cover slidably positioned over and around the housing and having an opening;

splines with the opening for engaging the hub of the needle; and retaining means within the housing for retaining the needle.

13. The safety device of claim 12 wherein the cover and housing are relatively slidably displaceable in the direction of the needle.

14. The safety device of claim 12 wherein the cover is generally cylindrical and the needle, cover, splines and opening are concentric.

15. The safety device of claim 12 wherein the retaining means are included within a chassis slidable into the housing.

16. The safety device of claim 12 further comprising ribs n the outside of the cover.

17. The safety device of claim 12 wherein the cover and the syringe have approximately equal diameters.

* * * * *